United States Patent
Harale et al.

(10) Patent No.: US 9,393,540 B2
(45) Date of Patent: Jul. 19, 2016

(54) HYDROPHILIC MEMBRANE INTEGRATED OLEFIN HYDRATION PROCESS

(71) Applicant: Saudi Arabian Oil Company, Dhahran (SA)

(72) Inventors: Aadesh Harale, Abqaiq (SA); Wei Xu, Dhahran (SA); Ibrahim Abba, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 14/516,822

(22) Filed: Oct. 17, 2014

(65) Prior Publication Data

US 2015/0037218 A1    Feb. 5, 2015

Related U.S. Application Data

(62) Division of application No. 13/705,360, filed on Dec. 5, 2012, now Pat. No. 8,921,619.

(60) Provisional application No. 61/566,839, filed on Dec. 5, 2011.

(51) Int. Cl.
  *B01J 8/00*   (2006.01)
  *B01J 14/00*  (2006.01)
  (Continued)

(52) U.S. Cl.
  CPC  *B01J 14/00* (2013.01); *B01J 8/009* (2013.01); *B01J 8/0453* (2013.01); *B01J 8/0492* (2013.01); *B01J 14/005* (2013.01);
  (Continued)

(58) Field of Classification Search
  CPC ..................................................... B01J 8/009
  See application file for complete search history.

(56) References Cited

U.S. PATENT DOCUMENTS

| | | | |
|---|---|---|---|
| 2,477,380 | A | 7/1949 | Kreps et al. |
| 3,994,983 | A | 11/1976 | Webers et al. |

(Continued)

FOREIGN PATENT DOCUMENTS

| | | |
|---|---|---|
| EP | 0210055 A1 | 1/1987 |
| WO | 2010116335 A1 | 10/2010 |

(Continued)

OTHER PUBLICATIONS

International Search Report with Written Opinion issued in related PCT Patent Application No. PCT/US2012/067891; dated May 28, 2013; 12 pages.

*Primary Examiner* — Lessanework Seifu
(74) *Attorney, Agent, or Firm* — Bracewell LLP; Constance G. Rhebergen; Kevin R. Tamm

(57) ABSTRACT

A membrane-integrated hydration reactor that is operable to produce an associated alcohol product from an olefin using water includes a solid acid olefin hydration catalyst in a production zone and a hydrophilic membrane operable to selectively permit pervaporation of water one-way and not permit pervaporation of the associated alcohol or permeation of the olefin at olefin hydration process conditions in a separations zone. The production zone is operable to form a production zone product mixture made of the associated alcohol and any unreacted water. The associated separations zone is operable to form and produce both the associated alcohol product and a pervaporated water product from the production zone product mixture. A method of olefin hydration for forming an associated alcohol product from an olefin using water uses the membrane-integrated hydration reactor at olefin hydration process conditions.

19 Claims, 3 Drawing Sheets

(51) Int. Cl.
  *C07C 29/04* (2006.01)
  *B01J 19/00* (2006.01)
  *C07C 29/74* (2006.01)
  *C07C 29/76* (2006.01)
  *B01J 8/04* (2006.01)
  *C07C 29/17* (2006.01)

(52) U.S. Cl.
  CPC ............ *B01J 19/0053* (2013.01); *C07C 29/04* (2013.01); *C07C 29/172* (2013.01); *C07C 29/74* (2013.01); *C07C 29/76* (2013.01); *Y02P 20/582* (2015.11)

(56) References Cited

U.S. PATENT DOCUMENTS

| | | | |
|---|---|---|---|
| 4,307,257 A | 12/1981 | Sada et al. | |
| 4,579,984 A | 4/1986 | Neier et al. | |
| 4,876,403 A | 10/1989 | Cohen et al. | |
| 4,956,506 A | 9/1990 | Latimer | |
| 5,146,009 A | 9/1992 | Cohen et al. | |
| 5,672,782 A | 9/1997 | Hattori et al. | |
| 7,141,707 B2 | 11/2006 | Beckmann et al. | |
| 7,235,704 B2 | 6/2007 | Grund et al. | |
| 7,709,690 B2 | 5/2010 | Endoh et al. | |
| 2009/0057224 A1 | 3/2009 | Huang et al. | |
| 2009/0118551 A1 | 5/2009 | Buijs et al. | |
| 2009/0253945 A1 | 10/2009 | Endoh et al. | |
| 2012/0108841 A1 | 5/2012 | Tenedorio Matos Da Silva et al. | |

FOREIGN PATENT DOCUMENTS

| | | |
|---|---|---|
| WO | 2011001285 A1 | 1/2011 |
| WO | 2012095744 A2 | 7/2012 |
| WO | 2013022565 A1 | 2/2013 |

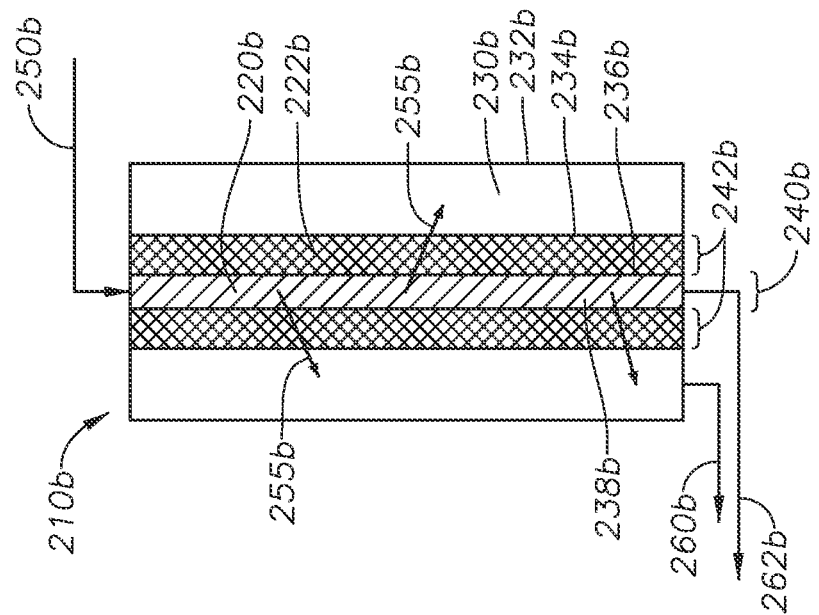
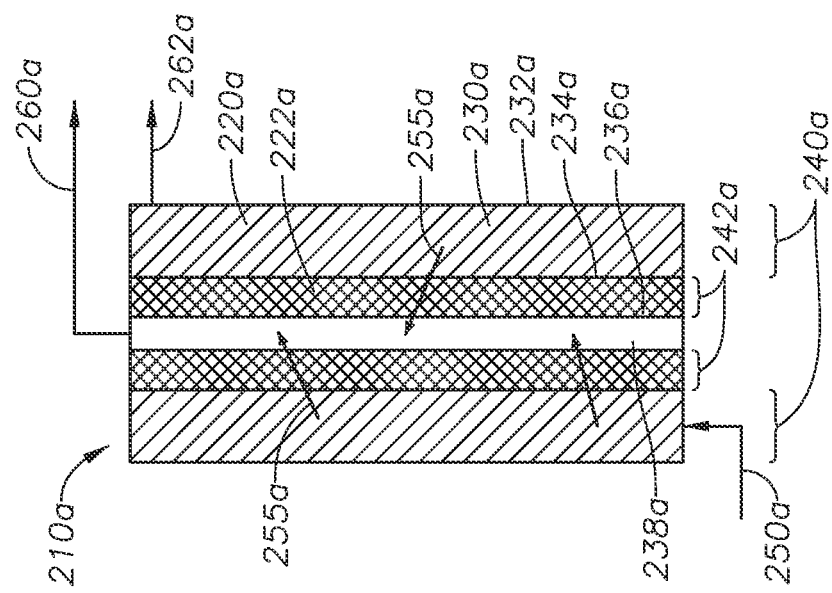

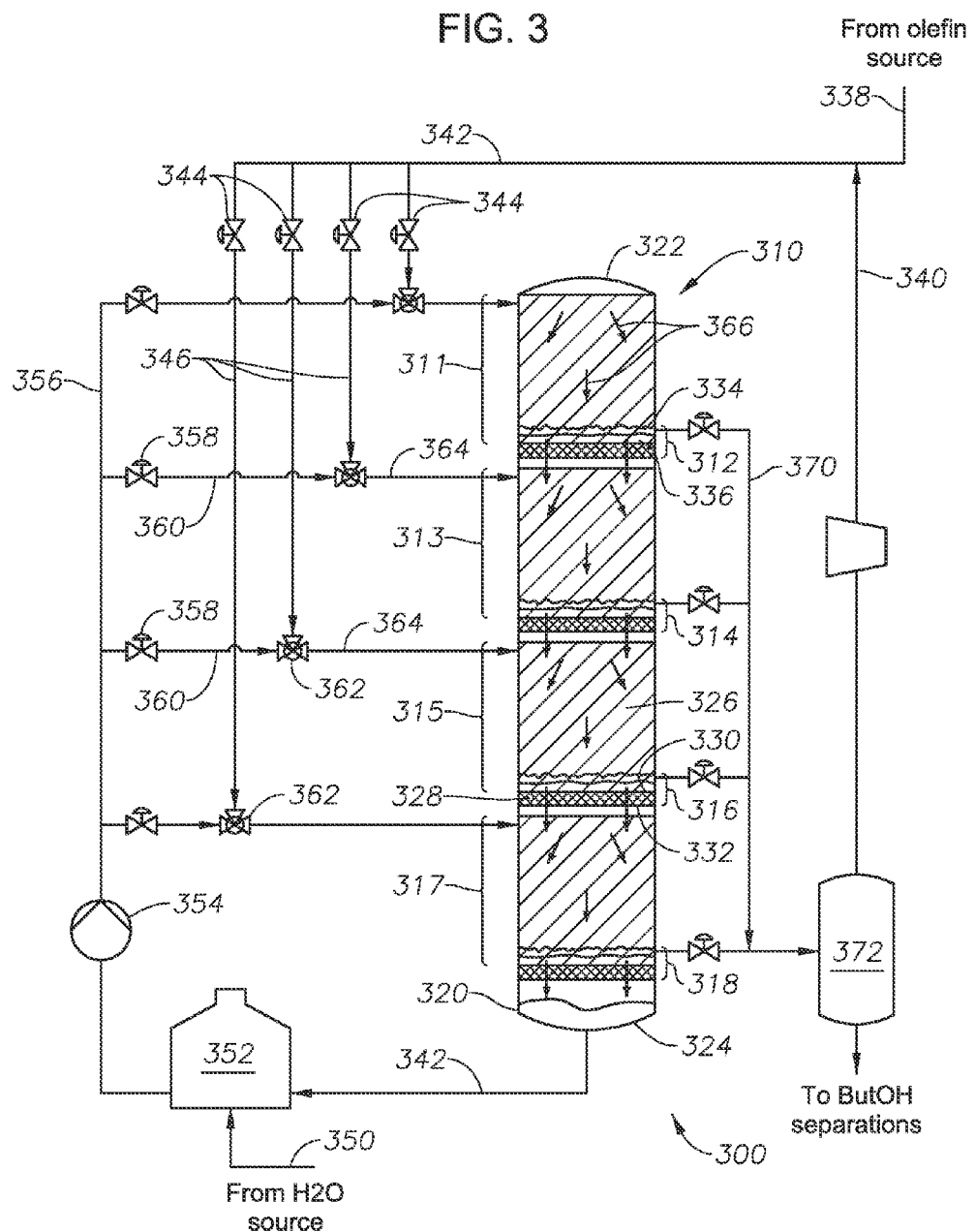

180
HYDROPHILIC MEMBRANE INTEGRATED OLEFIN HYDRATION PROCESS

CROSS-REFERENCE TO RELATED PATENT APPLICATIONS

This application is a continuing application of U.S. patent application Ser. No. 13/705,360 filed on Dec. 5, 2012 that claims priority from U.S. Provisional Application No. 61/566,839, filed Dec. 5, 2011. For purposes of United States patent practice, this application incorporates the contents of the Provisional Application by reference in its entirety.

BACKGROUND OF THE INVENTION

1. Field of the Invention

The field of invention relates to a system and process for the production of alcohols. More specifically, the field of invention relates to direct catalytic hydration of olefins to produce associated alcohols.

2. Description of the Related Art

The hydration of olefins to alcohols, and specifically the hydration of butenes to butanols, is a commercially important reaction. Alcohols from olefins have several important industrial applications. Alcohols, including butanols, are both solvents and chemical intermediaries for producing ketones, esters and ethers. Butanols are potentially useful as gasoline fuel-blending additives, which is a significant consumer market. Butanols can act as a fuel expander, an octane booster and an oxygenator similar to the roles played currently by ethanol and MTBE.

In spite of the currently available processes, there is no particularly effective route to produce mixed butanols economically. Many processes require pretreating feeds to isolate specific types of butenes. The conversion reactions often form mixtures of alcohols with water that require separate separations steps. The single-pass conversion rate for olefin hydration is very low—less than 10% in some cases.

SUMMARY OF THE INVENTION

A membrane-integrated hydration reactor that is operable to produce an associated alcohol product from an olefin using water includes a solid acid olefin hydration catalyst. The solid acid olefin hydration catalyst is operable to convert the olefin into its associated alcohol using water at olefin hydration process conditions. The hydration reactor also includes a hydrophilic membrane having a feed side and a permeate side. The hydrophilic membrane is operable to selectively permit pervaporation of water one-way from the feed side to the permeate side at olefin hydration process conditions. The pervaporation of water forms a pervaporated water product on the permeate side of the hydrophilic membrane. The hydrophilic membrane is not operable to permit pervaporation of the associated alcohol or permeation of the olefin at olefin hydration conditions. The hydration reactor also contains a production zone that contains the solid acid olefin hydration catalyst. The production zone is operable to receive an olefin feed containing the olefin and a water feed containing the water. The olefin and the water intimately intermingle in the presence of the solid acid olefin hydration catalyst. The production zone is operable to form a production zone product mixture made of the associated alcohol and any unreacted water. The production zone also passes the production zone product mixture to an associated separations zone. The hydration reactor also includes an associated separations zone that contains the hydrophilic membrane. The associated separa-tions zone fluidly couples to the production zone such that the production zone product mixture is directed to the feed side of the hydrophilic membrane. The associated separations zone is operable to form and produce both the associated alcohol product and the pervaporated water product from the production zone product mixture.

A method of olefin hydration for forming an associated alcohol product from an olefin using water in a membrane-integrated hydration reactor includes the step of introducing an olefin feed composition into the production zone of the hydration reactor. The olefin feed composition includes at least one isomer of butene. The method includes the step of introducing water into the production zone. The method includes the step of operating the membrane-integrated hydration reactor such that the associated alcohol forms from the olefin feed composition using water in the presence of a solid acid olefin hydration catalyst in the production zone. The method also includes the step of operating the hydration reactor such that the production zone product mixture forms from the mixing of the associated alcohol and any unreacted water in the production zone. The method also includes the step of operating the hydration reactor such that the production zone passes the production zone product mixture to the associated separations zone. The method also includes the step of operating the hydration reactor such that the associated separations zone selectively removes any unreacted water from the production zone product mixture. Removing the water from the production zone product mixture forms both the associated alcohol product and the pervaporated water product.

The membrane-integrated hydration reactor (MIHR) is operable to produce a mixed alcohol product from mixed olefins and water. Mixed alcohols are useful for both downstream industrial processes and in consumer applications, including as gasoline fuel additives, without additional separation or refinement. "Petro-butanols" can replace current octane-enhancing additives, including MTBE and refined ethanol, in gasoline.

The mixed olefins useful as a feedstock for the method of olefin hydration include at least one type of butene. The butene does not require pre-refining or separation to isolate the butene before introduction into the MIHR. Mixed olefins are relatively inexpensive as chemical feedstocks. Not requiring pretreatment or refining before use saves energy and avoids capital investment.

The membrane-integrated hydration reactor includes a solid acid olefin hydration catalyst in the production zone. "Solid catalyst" refers to non-water soluble materials that are operable to promote a chemical reaction. Solid acid olefin hydration catalysts remain inside each production zone of the MIHR. Examples of solid acid olefin hydration catalyst include ionic exchange resins, zeolites in acidic forms and acids supported on solid carriers. The method of olefin hydration using the MIHR does not require use of liquid acid as a catalyst. "Liquid acids" are acids that are soluble in aqueous solution. "Liquid catalysts" are heteropoly water-soluble liquid acids, including sulfuric acid and phosphoric acid. Liquid acids require regeneration or continuous addition. Liquid acids also can contaminate process water, which is desirable to reuse without excessive treatment.

Both the olefin hydration reaction and the separation process occur before the membrane-integrated hydration reactor produces the associated alcohol product. The MIHR promotes the hydration reaction, improves per-pass olefin conversion efficiency and improves overall process yield over traditional olefin hydration methods. The configuration and operation of the MIHR avoids the necessary use of external separations steps and equipment to remove water.

In instances where the membrane-integrated hydration reactor includes multiple production zones and separations zones, the continuous introduction of internally-recycled water from one production zone to another and the continuous removal of associated alcohols product not only shifts the olefin hydration reaction equilibrium in the production zones greatly towards the reaction products but also significantly improves butene conversion efficiency. Continuous associated alcohols product removal allows the olefin hydration reaction to proceed in the production zone, where the solid acid olefin hydration catalyst is present, beyond the equilibrium state versus batch-type processes.

The simultaneous production and separation processes occurring in each membrane-integrated hydration reactor directly produces a high-quality associated alcohols product that does not require additional processing before use. Additional processing downstream of the MIHR can extract desirable alcohols from the product, including mixed butanols, and especially specific butanols, including iso-butanol.

BRIEF DESCRIPTION OF THE DRAWINGS

These and other features, aspects, and advantages of the present invention are better understood with regard to the following Detailed Description of the Preferred Embodiments, appended Claims, and accompanying Figures, where:

FIGS. 2A and B are schematic diagrams of two embodiments of the membrane-integrated hydration reactor; and FIG. 3 is a schematic diagram of an embodiment of the membrane-integrated hydration reactor.

Figure 1:
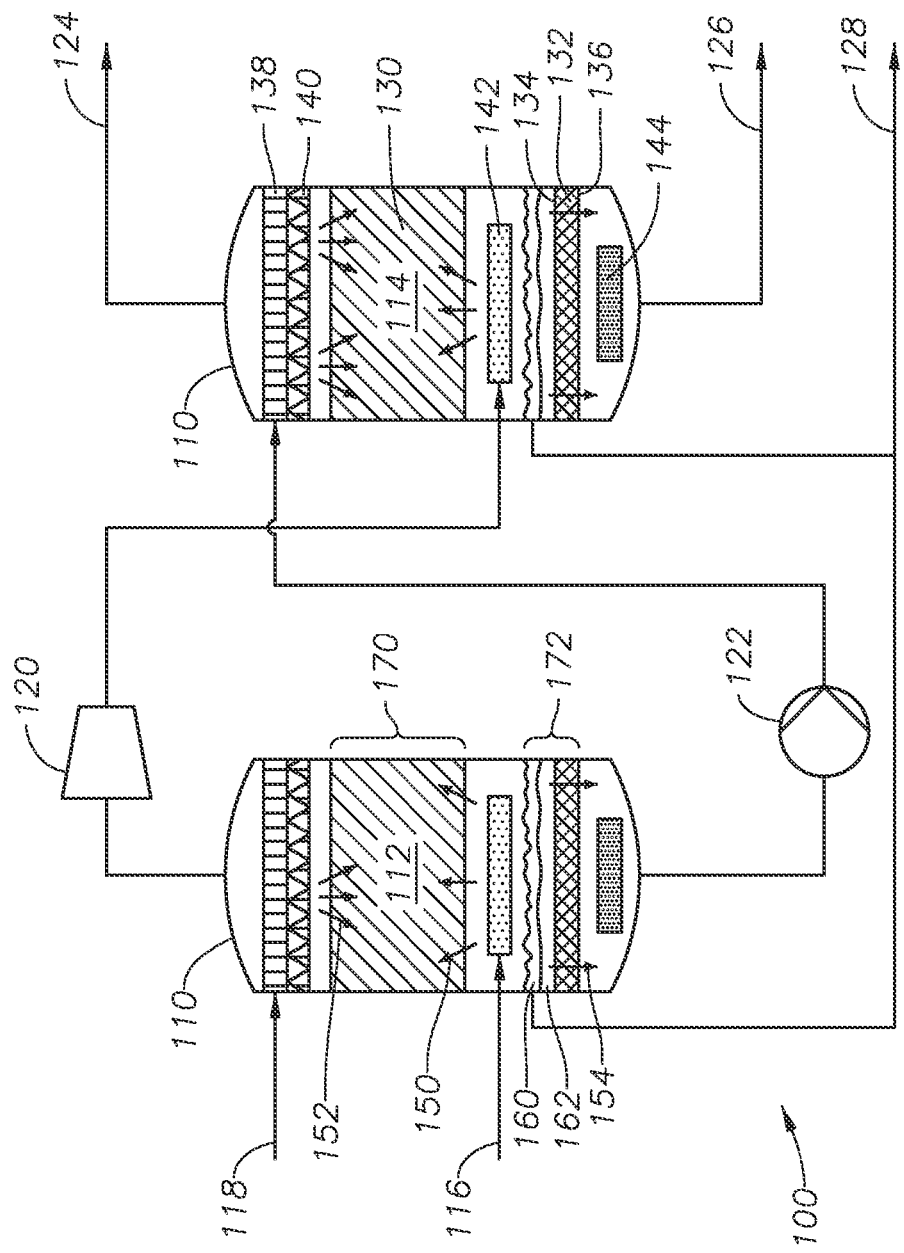
FIG. 1 is a schematic diagram of an embodiment of a first membrane-integrated hydration reactor coupled with a similar second membrane-integrated hydration reactor.

In the accompanying Figures, similar components or features, or both, may have the same or similar reference labels.

DETAILED DESCRIPTION OF THE PREFERRED EMBODIMENTS

The Specification, which includes the Summary of Invention, Brief Description of the Drawings and the Detailed Description of the Preferred Embodiments, and the appended Claims refer to particular features (including process or method steps) of the invention. Those of skill in the art understand that the invention includes all possible combinations and uses of particular features described in the Specification. Those of skill in the art understand that the invention is not limited to or by the description of embodiments given in the Specification. The inventive subject matter is not restricted except only in the spirit of the Specification and appended Claims.

Those of skill in the art also understand that the terminology used for describing particular embodiments does not limit the scope or breadth of the invention. In interpreting the Specification and appended Claims, all terms should be interpreted in the broadest possible manner consistent with the context of each term. All technical and scientific terms used in the Specification and appended Claims have the same meaning as commonly understood by one of ordinary skill in the art to which this invention belongs unless defined otherwise.

As used in the Specification and appended Claims, the singular forms "a", "an", and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced. The verb "couple" and its conjugated forms means to complete any type of required junction, including electrical, mechanical or fluid, to form a singular object from two or more previously non-joined objects. If a first device couples to a second device, the connection can occur either directly or through a common connector. "Optionally" and its various forms means that the subsequently described event or circumstance may or may not occur. The description includes instances where the event or circumstance occurs and instances where it does not occur. "Operable" and its various forms means fit for its proper functioning and able to be used for its intended use. "Associated" and its various forms means something connected with something else because they occur together or that one produces the other.

Spatial terms describe the relative position of an object or a group of objects relative to another object or group of objects. The spatial relationships apply along vertical and horizontal axes. Orientation and relational words including "upstream" and "downstream"; "above" and "below"; "up" and "down" and other like terms are for descriptive convenience and are not limiting unless otherwise indicated.

Where the Specification or the appended Claims provide a range of values, it is understood that the interval encompasses each intervening value between the upper limit and the lower limit as well as the upper limit and the lower limit. The invention encompasses and bounds smaller ranges of the interval subject to any specific exclusion provided. "Substantially free" means less than 1% by the indicated unit of measure.

Where the Specification and appended Claims reference a method comprising two or more defined steps, the defined steps can be carried out in any order or simultaneously except where the context excludes that possibility.

FIG. 1

FIG. 1 is a schematic diagram of an embodiment of a first membrane-integrated hydration reactor (MIHR) that couples with a similar embodiment of a second membrane-integrated hydration reactor. Olefin hydration system 100 includes two separate yet similar MIHRs 110: first reactor 112 and second reactor 114. For discussion proposes, similar internal apparatuses and processes occur in both reactors 112 and 114.

First reactor 112 and second reactor 114 couple together such that they operate in series. Olefin feed line 116 and water feed line 118 separately feed olefins and water, respectively, into first reactor 112. Unreacted olefins pass from the top of first reactor 112 into second reactor 114 via olefins compressor 120. Recovered water passes from the bottom of first reactor 112 to second reactor 114 via water pump 122. Leftover olefins line 124 and leftover water line 126 convey unused olefins and water from second reactor 114. Associated alcohols line 128 recovers associated alcohols product separately from both MIHRs 110.

Each MIHR 110 has several internal parts. Each MIHR 110 has fixed solid acid olefin hydration catalystbed 130; hydrophilic membrane 132 with feed side 134 and permeate side 136, respectively; water distributor 138 with nozzles 140; olefin sparger 142 and condenser 144. All parts of each MIHR 110 are on feed side 134 of hydrophilic membrane 132 except condenser 144, which is on permeate side 136. Fixed solid acid olefin hydration catalystbed 130 is operable to form associated alcohols using olefins and water at olefin hydration process conditions. Olefin sparger 142 is operable to distribute olefins into each MIHR 110 such that olefins contact fixed solid acid olefin hydration catalystbed 130 (arrows 150).

Water distributor 138 distributes water into fixed solid acid olefin hydration catalystbed 130 (arrows 152). Hydrophilic membrane 132 is operable to permit water to pervaporate from feed side 134 to permeate side 136 (arrows 154) at olefin hydration process conditions. Hydrophilic membrane 132 does not permit olefins or associated alcohols to pervaporate through hydrophilic membrane 132 at olefin hydration process conditions. Condenser 144 is operable to reduce the temperature of the permeate such that it condenses.

FIG. 1 shows a dual-layer liquid on top of feed side 134 of hydrophilic membrane 132: layer of associated alcohols 160 saturated with water floats on top of layer of water 162 saturated with associated alcohols.

Production zone 170 for each MIHR 110 extends to include where water and olefins can form associated alcohols. Production zone 170 is where olefins intimately intermingle with water and convert into associated alcohols and includes fixed solid acid olefin hydration catalystbed 130. Separations zone 172 for each MIHR 110 extends to where water and associated alcohols separate from one another not only through chemical incompatibilities (that is, immiscibility) but also by action of hydrophilic membrane 132 extracting water from layer of water 162. Production zone 170 and separations zone 172 couple together but do not contact each other. Reaction products and unused water flow from production zone 170 to separations zone 172 inside MIHR 110.

FIG. 1 is useful for discussing steps in the method of olefin hydrolysis using an embodiment membrane-integrated hydration reactor. Olefin feed line 116 introduces olefins and water feed line 118 introduces water separately into first reactor 112. At typical reaction conditions, water is a liquid and olefins are vaporous. Feed olefins and water traverse in generally opposing directions within each MIHR 110 and permeate into fixed solid acid olefin hydration catalyst bed 130. On the surface of the solid acid olefin hydration catalyst, the olefins and water intimately mix and react to form associated alcohols.

The associated alcohols, along with any excess water present in production zone 170, form a production zone product mixture within fixed solid acid olefin hydration catalyst bed 130, which migrates downward through solid acid olefin hydration catalyst bed 130 due to gravity and passes from production zone 170. The production zone product mixture flows into separations zone 172, where the associated alcohols and water separate. Associated alcohols form layer of associated alcohols 160, which passes from MIHR 110 as associated alcohols product into associated alcohol line 128. Water from layer of water 162 pervaporates through hydrophilic membrane 132 by absorbing onto feed side 134, diffusing through and desorbing from hydrophilic membrane 132 as a permeate vapor on permeate side 136, forming a pervaporated water product. Upon desorption, condenser 144 liquefies pervaporated water product.

Olefin hydration process 100 passes condensed permeate water from first reactor 112 to second reactor 114 using water pump 122. Condensed permeate water passes from the bottom of second reactor 114 and out of olefin hydration process 100 via leftover water line 126. Unreacted olefins pass out of the top of MIHR 110. Olefin hydration process 100 passes unreacted olefins from first reactor 112 to second reactor 114 as a feed using olefin compressor 120 as a feed. Unreacted olefins from second reactor 114 pass out of olefin hydration process 100 via leftover olefins line 124. Both leftover water line 126 and leftover olefins line 124 can route back to water feed line 118 and olefin feed line 116, respectively.

Pressure in production zone 170 and pressure differential across hydrophilic membrane 132 in separations zone 172 drive several of the simultaneous processes that occur in MIHR 110. Elevated pressure keeps the water and associated alcohols in the liquid phase and olefins in the vapor phase, allowing both gravity and buoyancy to not only separate the liquids from the gases but also to separate the immiscible liquids in the production zone product mixture into layer of associated alcohols 160 and layer of water 162 in separations zone 172. Condenser 144 causes the formation of liquid water on permeate side 136 of hydrophilic membrane 132, lowering the pressure on that side of hydrophilic membrane 132. Lowering the pressure on permeate side 136 increases the pressure drive through hydrophilic membrane 132, removing additional water from feed side 134. Removal of water from water layer 162 shifts the water/associated alcohol concentration away from equilibrium in layer of water 162, driving associated alcohols from layer of water 162 into layer of associated alcohols 160. This further improves recovery of the associated alcohols and quality of the associated alcohols product.

FIG. 2

FIGS. 2A and B are schematic diagrams of two embodiments of the membrane-integrated hydration reactor. FIGS. 2A and B show sectional views of membrane-integrated hydration reactors (MIHRs) 210a and 210b, respectively, in a generally tubular configuration.

In FIG. 2A, MIHR 210a contains both solid acid olefin hydration catalyst 220a and hydrophilic membrane 222a. Solid acid olefin hydration catalyst 220a fills annular volume 230a formed between outer shell 232a and outer surface 234a of hydrophilic membrane 222a. Hydrophilic membrane 222a also has inner surface 236a which defines a void interior fluid conduit 238a.

Production zone 240a for MIHR 210a is annular volume 230a. Separations zone 242a is hydrophilic membrane 222a. Production zone 240a and separations zone 242a directly contact one another as solid acid olefin hydration catalyst 220a contacts outer surface 234a of hydration membrane 222a. The tubular configuration of MIHR 210a does not allow standing layers of liquid on outer surface 234a.

A combined water and olefins feed enters annular volume 230a through feed conduit 250a. The water and olefins in production zone 240a intimately intermingle and contact solid acid olefin hydration catalyst 220a, forming associated alcohols at olefin hydration process conditions and with any excess water forms the production zone product mixture. The excess water separates from the production zone product mixture moving through annular volume 230a by passing through hydrophilic membrane 222a (see arrows 255a). Water passes from MIHR 210a using water outlet conduit 260a. Associated alcohols conduit 262a produces associated alcohols product.

In FIG. 2B, MIHR 210b is similar to 210a except that solid acid olefin hydration catalyst 220b fills interior fluid conduit 238b rather than annular volume 230b. Annular volume 230b is a void space in MIHR 210b. Production zone 240b is interior fluid conduit 238b.

A combined water and olefins feed enters interior fluid conduit 238b through feed conduit 250b. The water and olefins in interior fluid conduit 238b intimately intermingle and contact solid acid olefin hydration catalyst 220b, forming associated alcohols and with excess water the production zone product mixture. Water separates from the production zone product mixture traversing production zone 240b by passing through hydrophilic membrane 222b (see arrows 255b) into annular volume 230b. Water passes using water outlet conduit 260b. Associated alcohols conduit 262b produces associated alcohols product.

FIG. 3

FIG. 3 is a schematic diagram of an embodiment of the membrane-integrated hydration reactor as part of an olefin hydration process. Olefin hydration system 300 includes membrane-integrated hydration reactor (MIHR) 310 having four separate production zones (311, 313, 315, 317) and four separate associated separations zones (312, 314, 316, 318) that couple to one another in an alternating, vertical relationship within outer vessel wall 320. MIHR 310 has top 322 and bottom 324.

Each production zone (311, 313, 315, 317) has solid acid olefin hydration catalyst bed 326 of unstructured catalyst. Each associated separations zone (312, 314, 316, 318) includes hydrophilic membrane 328. Hydrophilic membrane 328 has feed side 330 and permeate side 332. FIG. 3 shows solid acid olefin hydration catalyst bed 326 for production zones 311, 313, 315, and 317 contacting feed side 322 of hydrophilic membrane 328 of associated separations zones 312, 314, 316, and 318, respectively. Solid acid olefin hydration catalyst bed 326 in production zones 313, 315 and 317 almost touches permeate side 332 of hydrophilic membrane 328 of associated separations zone 312, 314 and 316, respectively, above each to maximize the volume of production zones 313, 315 and 317. Solid acid olefin hydration catalyst bed 326 in production zones 311 almost contacts top 332. The position of solid acid olefin hydration catalyst bed 326 relative to each hydrophilic membrane 328 results in production zones 311, 313, 315 and 317 overlapping with associated separations zones 312, 314, 316 and 318, respectively. The position of both layer of associated alcohol 334 and layer of water 336 on top of each hydrophilic membrane 328 is within the area of overlap between production zones 311, 313, 315 and 317 and associated separations zones 312, 314, 316 and 318, respectively, and causing layers 334 and 336 to intermingle with the lower portion of solid acid olefin hydration catalyst bed 326.

Olefin feed to membrane-integrated hydration reactor 310 originates from two sources: fresh olefins from make-up olefin feed line 338 and recovered olefins from recycle olefin feed line 340. Olefin feed header 342 combines the two olefins sources into a single feed line. Olefin feed control valves 344 regulate the amount of olefins introduced into each production zone (311, 313, 315, 317) through olefin feed lines 346.

Water feed to membrane-integrated hydration reactor 310 originates from two sources: make-up water from water make-up feed line 348 and recycled water from water recycle line 350. Both lines feed into water storage tank 352. Water feed pump 354 conveys water to water feed header 356. Water feed control valves 358 regulate the amount of water introduced to each production zone (311, 313, 315, 317) through water feed lines 360.

Water from water feed lines 360 and olefins from olefin feed lines 346 are forcibly mix in feed mixers 362 and pass into production zones (311, 313, 315, 317) using combined feed line 364.

Within each production zone (311, 313, 315, 317) olefins and water intimately contact the solid acid olefin hydration catalyst bed 326. At olefin hydration process conditions, the olefins and water while in the presence of the solid acid olefin hydration catalyst form associated alcohols. The associated alcohols and excess water combine to form the production zone product mixture, which trickles downward through solid acid olefin hydration catalyst bed 326 (arrows 366) and pools on feed side 330 of hydrophilic membrane 328. While on feed side 330, the production zone product mixture separates and forms the dual-layer liquid of layer of associated alcohol 334 on top of layer of water 336. Both layers 334 and 336 are located in both production zones (311, 313, 315, 317) and separations zones (312, 314, 316, 318). Any butene entrained in layer of water 336 converts into associated alcohols.

Production zone 311 is in one-way fluid communication with production zone 313 through hydrophilic membrane 328 of separations zone 312. Water not consumed by the olefin hydration reaction into production zone 311 pervaporates through hydrophilic membrane 328 into production zone 313. Upon desorbing into production zone 313, the pervaporated water acts as a reactant in the olefin hydration reaction just as the water introduced through combined feed line 364. Production zone 313 is in one-way fluid communication with production zone 315 through separations zone 314. Production zone 315 is in one-way fluid communication with production zone 317 through separations zone 316. Portions of the water introduced into production zones 311, 313 and 315 can traverse through MIHR 310 and enter production zone 317 through separations zone 316.

Water not consumed in the olefin hydration process in production zone 317 pervaporates through hydrophilic membrane 328 of separations zone 318 and collects in bottom 324. Water recycle line 342 conveys the collected water to water storage tank 352.

A continuous portion of layer of associated alcohol 334 from each separations zone (312, 314, 316, 318) passes out of membrane-integrated hydration reactor 310 as associated alcohols product through product fluid conduits 370. Alcohol separations pot 372 flashes off any dissolved olefins from the associated alcohols product. Recycle olefin feed line 340 compresses and recycles the recovered olefins from alcohol separations pot 372 for reintroduction into MIHR 310. The degassed associated alcohols product passes to downstream systems outside of olefin hydration system 300.

Butene and Olefin Reactants

The olefin composition feed enters the membrane-intergrated hydration reactor as a vapor. An embodiment of the method of olefin hydration includes introducing a single isomer of butene as the olefin feed composition. Butenes have four isomeric structures, as seen in Structures 1-4:

(St.1)

1-butene

(St.2)

cis-2-butene

, and
(St.3)

trans-2-butene

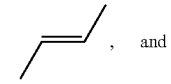
(St.4)

iso-butene

An embodiment of the method of olefin hydration includes introducing a mixture of butene isomers as the olefin feed composition. "Mixed butenes" refers to mixtures of butenes with more than one isomeric structure, including all four types of butenes. Mixed butenes have a boiling temperature in a range of from about −7° C. to about 4° C. at atmospheric pressure depending on the relative ratio and types of isomers present.

An embodiment of the method of olefin hydration includes introducing a mixture of lower-carbon olefins as the olefin feed composition. A single butene isomer composition or mixed butenes combined with other non-butene olefins forms "mixed olefins." Mixed olefins are "lower-carbon olefins", which are olefins having two to six carbon atoms. Ethylene, propene, butenes, pentenes, and hexenes are lower-carbon olefins. Lower-carbon olefins are not aromatic.

A number of sources can provide suitable mixed butenes or mixed olefins for the olefin hydration process. A fluidized catalytic cracker (FCC) unit is a potential source. The product stream from a steam catalytic cracker, after extracting butadienes, can act as a source. Potential sources of pure isomers of butene, mixed butenes and mixed olefins having lower carbons include MTBE (methyl-tert-butyl ether), SBA (sec-butyl alcohol) and TBA (tert-butyl alcohol) production units.

Water Reactant

The olefin hydration process uses water to effect direct hydration. Fresh make-up water sources include tap water, deionized water, distilled water, boiler feed water (BFW) and steam condensate. Pretreating water for pH and demineralizing it prevents inorganic buildup and scale in the membrane-integrated hydration reactor.

Recycled permeate water from the separations zone in the membrane-integrated hydration reactor is also an excellent source of feed water. The olefin hydration process maximizes the use of water by recycling. Water permeating through a hydrophilic membrane is substantially free of olefins, associated alcohols and other impurities.

Pre-Combined Feed Mixer

An embodiment of the olefin hydration process includes forcibly combining water and the feed olefins into a combined feed stream before introducing the immiscible combination into the membrane-integrated hydration reactor. A mixing device, for example a gas sparger or a venturii nozzle, incorporates the olefins into the water feed such that the two immiscible materials turbulently mix. The mixing device is operable such that the two immiscible materials intimately contact one another for a sufficient time to permit introduction of the combined stream into the production zone of the MIHR.

Membrane-Integrated Hydration Reactor

The membrane-integrated hydration reactor is operable to convert olefins, especially butenes, into their associated alcohols, especially butanols, through direct hydration reactions in the presence of the solid acid olefin hydration catalyst.

Production and Separations Zones

The olefin hydration reaction occurs in the production zone of the membrane-integrated hydration reactor. The production zone contains the solid acid olefin hydration catalyst in the MIHR. The production zone is the area where olefins and water convert into associated alcohols during the olefin hydration process. This formation of the associated alcohols occurs in the presence of the solid acid olefin hydration catalyst, which is present in the production zone. The production zone also forms a product mixture comprising the associated alcohols and any unreacted water. The production zone product mixture forms within the structure of the solid acid olefin hydration catalyst. The production zone passes the production zone product mixture to the associated separations zone for separating the water from the associated alcohols.

Each production zone couples with an associated separations zone. The production zone associated with an associated separations zone passes production zone product mixture, which contains the associated alcohols with any excess water. The associated separations zone couples such that the production zone product mixture is directed to the feed side of the hydrophilic membrane of the associated separations zone. A production zone coupled to the permeate side of a hydrophilic membrane of a separations zone is not associated with the separations zone because it is not operable to pass water or associated alcohols to the feed side of the hydrophilic membrane.

An embodiment of the membrane-integrated hydration reactor is operable to maintain separate operating conditions between the production zone and the associated separations zone. A partition between the production zone and the associated separations zone can permit maximization of local olefin hydration production properties in the production zone (high pressure) while permitting maximization of local production zone product mixture separation (for example, maintaining a high-pressure gradient across the hydrophilic membrane). The partition maintains the coupling of the production zone with the associated separations zone.

The associated separations zone is operable to form the associated alcohols product from the production zone product mixture by removing the excess water before producing them. Any excess water in the membrane-integrated hydration reactor passes from the separations zone by selective extraction via the hydrophilic membrane. The extracted water either passes to another production zone or is removed from the MIHR as a pervaporated water product. Optionally, physical separation of the production zone product mixture due to gravity and immiscibility can occur in the separations zone. The configuration of the MIHR can allow a two layer liquid to form in the separations zone from the production zone product mixture: an associated alcohol-rich layer and a water-rich layer. The associated alcohols, being both less dense and not miscible beyond several percent in water, float on top of the water layer. Water saturates the formed associated alcohol layer and associated alcohols saturates the formed water layer.

Removal of water from the separations zone using a hydrophilic membrane has three useful effects. First, extracting water from a water layer in contact with the feed side of the hydrophilic membrane changes the compositional equilibrium of the water layer. Removing water drives associated alcohols dissolved in the water layer out of the water layer to reestablish the water/alcohol compositional equilibrium. This improves the quality of the associated alcohols: associated alcohols driven out of the water layer either transport into the associated alcohol layer or move freely towards extraction. Second, the cooling of the hydrophilic membrane through pervaporation reduces the temperature of both the water in contact with the feed side of the hydrophilic membrane, which eventually transports and cools other fluids, including associated alcohols layer, proximate to the feed side. The reduction in temperature reduces the absorption capacity of both associated alcohols and water for immiscible gases such as olefins. Finally, as previously described the pervaporated water is highly purified and suitable for immediate use as a reactant in another production zone.

An embodiment of the membrane-integrated hydration reactor has a production zone with an associated separations zone that overlaps within the reactor. Configurations of the solid acid olefin hydration catalyst, where the catalyst is in close proximity to or even in contact with the feed side of the hydrophilic membrane, can cause overlapping zones where separations and production can occur simultaneously. FIG. 3 shows an embodiment of the MIHR where this can occur upon formation of the water/associated alcohols layers on the feed side of the hydrophilic membrane.

An embodiment of the membrane-integrated hydration reactor has more than one production zone and more than one associated separations zone. An embodiment of a multiple production zone and associated separations zone hydration reactor includes where the more than one production zones and the more than one associated separations zones are alternating in series and fluidly couple to permit one-way fluid communications through the alternating series of production zones and associated separations zones. In such embodiments, the fluid of communication is water. The coupling of multiple production zones and associated separations zones within the same membrane-integrated hydration reactor in series permits expedient removal from the production zone of unused and recyclable reactants by extraction through the associated separations zone. The passing of unconverted olefins and any excess water improves operational efficiency, especially olefin conversion efficiency, and ensures conservation and continuous upgrading of water.

The associated separations zone can separate water and redistribute it efficiently into another fluidly coupled production zone as a pervaporate water product. Excess water introduced into the first production zone in the alternating series can travel the entire operating length of the membrane-integrated hydration reactor from the first production zone, through all the other production zones, and through all of the associated separations zones, and pass from the MIHR. The water is only operable to communicate one-way through the MIHR due to the configuration of the hydrophilic membranes, which only permit one-way fluid communication between the feed side and the permeate side. An embodiment of the membrane-integrated hydration reactor having the alternating series of fluidly coupled more than one production zones and more than one associated separations zones includes a configuration such that a production zone is operable to communicate fluid one-way to all of the remaining production zones and all of the separations zones in the series.

In an embodiment of the membrane-integration hydration reactor having an alternating series of fluidly coupled more than one production zones and more than one associated separations zones, the first production zone is in direct fluid contact only with one associated separations zone. In such an embodiment, the last associated separations zone in the alternating series is in direct fluid contact only with one production zone. In such an arrangement, all the other production zones are in direct fluid contact with more than one separations zones and all the other associated separations zones are in direct fluid contact with more than one production zones.

An embodiment of the membrane-integrated hydration reactor having more than one production zone is operable to maintain separate operating conditions between a first set of production and associated separations zones and a second set of production and associated separations zones, where the first associated separations zone is fluidly coupled to and in one-way fluid communications with the second production zone. A physical partition, for example, between sets of production and separations zones within a MIHR can permit the modification of operating conditions of a production zone or a separations zone without negatively affecting operations of coupled or downstream production or separations zones. A partition between a production zone and a non-associated separations zone that maintains one-way fluid communication between the non-associated separations zone and the production zone permits the manipulation of operating conditions such that, for example, a sub-atmospheric environment forms on the permeate side of the non-associated separations zone while maintaining a greater-than-atmospheric olefin hydration process pressure in the coupled downstream production zone while still receiving water communicated the upstream membrane.

An embodiment of the membrane-integrated hydration reactor includes where the number of hydrophilic membranes and the number of production zones are not the same.

Solid Acid Olefin Hydration Catalyst

The olefin hydration reaction occurs in the presence of solid acid olefin hydration catalyst. The olefin hydration reaction follows the formula of Equation 1:

$$\text{Olefin} + \text{Water} \rightarrow \text{Alcohol} \tag{Eq. 1}$$

For example, isobutene and water react in the presence of an acidic catalyst to form the associated tert-butanol (TBA) per Equation 2:

$$CH_2{=}C(CH_3)_2 + H_2O \rightarrow (CH_3)_3COH \tag{Eq. 2}$$

Also, 2-butenes react with water to form the associated sec-butanol (SBA) per Equation 3:

$$CH_3{-}HC{=}CH{-}CH_3 + H_2O \rightarrow CH_3CH(OH)CH_2CH_3 \tag{Eq. 3}$$

The membrane-integrated hydration reactor includes solid acid olefin hydration catalyst. The solid acid olefin hydration catalyst is any commercially available solid acid catalyst suitable for converting olefins, especially butenes, into their associated alcohols, especially butanols, with water. Examples of solid acid olefin hydration catalyst include acidic zeolites, $MoO_3/WO_3$, ion exchange resins and supported solid acid catalysts. An example of a supported solid acid olefin hydration catalyst is phosphoric acid supported on silica. Solid support carriers include silica, metal oxides, clays, zeolites and carbon black. Examples of suitable ion exchange resins that are solid acid olefin hydration catalyst include DOWEX® 50 (Dow Chemical; Midland, Mich.), AMBERLYST® 15 (Rohm & Haas; Philadelphia, PN), and D008 resin (KaiRui Chemical; China).

The solid acid olefin hydration catalyst facilitates fluid contact between the reactants as well as conveyance of the associated alcohols and excess water away from the production area. An embodiment of a membrane-integrated hydration reactor includes a solid acid olefin hydration catalyst in a packed or structured catalyst bed configuration. The reactants disperse into the packed or structured bed configuration, intimately intermingling while contacting the catalyst surface. An embodiment of a MIHR includes a solid acid olefin hydration catalyst in a loose catalyst bed configuration. An embodiment of a MIHR includes a solid acid olefin hydration catalyst integrated with the feed side surface of a hydrophilic membrane. Integration includes adhesion, infusion and coating on the feed surface of the hydrophilic membrane with the solid acid olefin hydration catalyst such that the selective permeation operability of the hydrophilic membrane is not disturbed.

Hydrophilic Membrane

Membranes are thin, solid physical barriers that selectively permit transport through the barrier of some chemical constituents but not others. Given a mixture of components in a fluid used with a membrane, the concentration of the component that passes through the membrane—the permeate—increases as other components of the mixture cannot pass through the membrane. Both the chemical and the physical nature of the membrane material controls the type and rate of flux of the permeate component through the membrane at a given set of olefin hydration conditions. The concentration of the components that cannot pass through the membrane—the retentate—also improves in quality as the amount of water diminishes in the retentate while still in the membrane-integrated hydration reactor.

In the membrane-integrated hydration reactor, the hydrophilic membrane is operable to permit pervaporation of water at olefin hydration operating conditions, forming a pervaporated water product. The hydrophilic membrane is also operable to not permit pervaporation of associated alcohols and to not permit permeation of olefins at olefin hydration conditions.

Hydrophilic membranes attract water molecules. Although not intending to be bound by theory, it is believed that water, having an affinity to the hydrophilic membrane, contacts and accumulates at the water-solid interface of the hydrophilic membrane to crowd out other mixture components. Once formed, the hydrogen bonding between water and the hydrophilic membrane is stable. In addition, the build-up of water on the hydrophilic membrane feed side prevents hydrophobic substances from contacting the surface of the membrane. Associated alcohols above several percent in the aqueous solution and olefins in general are immiscible water; therefore, they do not dissolve in the water layer and migrate to the feed surface of the membrane in large enough amounts to interfere with the pervaporation of water.

"Pervaporation" refers to a liquid membrane separation process. Water adsorbs onto the feed surface of the hydrophilic membrane, solvates into the membrane material, diffuses through the membrane, and desorbs from the membrane on the permeate side as a vapor. The phase change that occurs between adsorbing onto the feed surface of the hydrophilic membrane and desorbing from the permeate side as a vapor cools the hydrophilic membrane, which in turn cools the retentate on the feed side of the hydrophilic membrane.

Operating conditions affect the amount of permeate that diffuses through the hydrophilic membrane. A change in conditions in a first production zone affects the rate of flux through the shared hydrophilic membrane received by a second production zone. The partial pressure difference between the feed side water vapor pressure and the permeate side water vapor pressure is the driving force for water pervaporation through the hydrophilic membrane. As partial differential pressure decreases between the feed and permeate sides, the flux across the membrane declines. Decreasing the pressure on the permeate side of the hydrophilic membrane increases flux through the hydrophilic membrane. Means of inducing lower pressure on the permeate side includes using a pump or a compressor to forcibly withdraw permeate vapor or condensed fluid from the permeate side of the hydrophilic membrane. A condenser on the permeate side also reduces the operating pressure on the permeate side by causing pervaporation permeate vapor to condense. Elevating the introduction pressure of olefins and water feeds can also have the same effect. It is also known that for pervaporation processes the temperature of the feed fluid increases the flux through the membrane. Elevating the production zone temperature increases the flux rate of water through the hydrophilic membrane.

The macro form of the hydrophilic membrane can take any physical forms. Example physical forms include tubular, film, hollow fiber and strand, woven web, nonwoven web, flat sheet, tubular-shaped, plate and spiral-wound layered cylinders. As an elastic material, the hydrophilic membrane can attach to a pre-formed frame inserted between two separation and production zones of the membrane-integrated hydration reactor, act as the common boundary between the two zones, and permit one-way fluid communication from one zone to the other. The hydrophilic membrane is operable as both a physical blockade and a chemical barrier between coupled production zones or a production zone and a permeate removal system except to water.

An embodiment of the membrane-integrated hydration reactor includes hydrophilic membranes made of inorganic material. Inorganic materials are non-organic materials that include ceramics, metals, mixed metal oxides (MMOs) and glass. Inorganic membranes are highly resistant to cleaning chemicals and resist corrosive liquids and gases, including aqueous and solid acids, at elevated operating temperatures for prolonged periods. Inorganic membranes can operate at temperatures in excess of over 1000° C. Example inorganic membrane materials include zeolites, which include silicalite-1, Ge-ZSM-5, B-type and ZSM-11.

An embodiment of the membrane-integrated hydration reactor includes hydrophilic membranes made of polymeric material. Polymeric membranes include glassy polymeric materials (that is, prepared at temperatures below the glass transition temperature) and rubbery polymeric materials (that is, prepared at temperatures above the glass transition temperature). Rubbery polymers typically demonstrate increased component flux and lower component selectivity than glassy materials. The physical configuration of polymeric membranes includes woven and non-woven membranes.

Polymer materials suitable for comprising at least part of a hydrophilic membrane include polyolefins, poly(isoprenes), poly(butadienes), fluorinated polymers, chlorinated polymers, polyesters, polyamides, polyimides, polyethers, sulfonated and non-sulfonated poly(ether sulfones), poly(sulfones), polyphenylene oxides, polyphenylene sulfides, poly(vinyl acetates), copolymers of vinyl acetate, poly(phosphazenes), poly(vinyl esters), poly(vinyl ethers), poly(vinyl alcohols), poly(carbonates), polystyrenes and silicone rubbers.

An embodiment of the membrane-integrated hydration reactor includes hydrophilic membranes made of a composite of both inorganic and polymeric materials. Such hydrophilic membranes can possess advantageous properties of both inorganic and polymeric materials. The composite hydrophilic membrane can include at least one layer of polymer membrane material and at least one layer of inorganic membrane material.

Other Production Zone and Separations Zone Apparatuses

Nozzles, spargers and sprayers are examples of equipment that can distribute separate or combined olefin and water feeds into a production zone of the membrane-integrated hydration reactor. Chilled collection and distributor plates located proximate to the permeate surface of the hydrophilic membrane can condense and redistribute permeate water into a downstream coupled production zone or to water handling systems outside of the MIHR. The design and configuration of any internal distribution system should distribute water and olefins into the solid acid olefin hydration catalyst to maximize the loading of the reactant materials.

A membrane-integrated hydration reactor can include an internal condenser. The configuration of the condenser can be physically internal to the MIHR or externally connected through conduits to the interior of the separations zone. An embodiment of the MIHR includes an internal condenser operable to condense into a liquid the pervaporated water product on the permeate side of the hydrophilic membrane. The condensation of the permeate vapor in the vapor-receiving production zone increases the flux gradient across the hydrophilic membrane and liquefies the vapor for distribution into the solid acid olefin hydration catalyst.

Associated Alcohols

The types of associated alcohols made in the production zone are associated with the olefins used as the feed. An embodiment of the method of olefin hydration produces associated alcohols of a single isomer of butanol. Butanols formed in the production zones via olefin hydration of butenes include Structures 5-8:

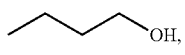

1-butanol (n-butanol) (St.5)

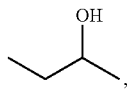

2-butanol (sec-butyl alcohol; SBA) (St.6)

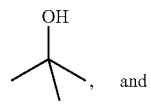

2-methyl-2-propanol (tert-butanol; TBA) (St.7)

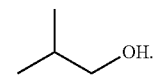

2-methyl-1-propanol (iso-butanol) (St.8)

An embodiment of the method of olefin hydration produces associated alcohols of mixed isomers of butanol. "Mixed butanols" refer to a product composition that includes more than one isomer of butanol, including all four isomers of butanol. Mixed butanols have a boiling temperature in a range of from about 82° C. to about 118° C. depending on the relative ratio and types of isomers present. An embodiment of the method of olefin hydration includes operating the membrane-integrated hydration reactor such that mixed butanols comprising TBA, SBA, or both, form.

An embodiment of the method of olefin hydration includes where the associated alcohol formed is a mixture of lower-carbon alcohols. "Mixed alcohols" refers to the product composition that includes not only at least one isomer of butanol but also other lower-carbon (that is, 2-6 carbons) non-butanol alcohols. Non-butene olefins included in the reaction composition form their associated alcohol products, for example, propene forms propanols (normal and iso-).

Supporting Equipment

Embodiments include many additional standard components or equipment that enables and makes operable the described apparatus, process, method and system. Examples of such standard equipment known to one of ordinary skill in the art includes heat exchanges, pumps, blowers, reboilers, steam generation, condensate handling, membranes, single and multi-stage compressors, separation and fractionation equipment, valves, switches, controllers and pressure-, temperature-, level- and flow-sensing devices.

Operation, control and performance of portions of or entire steps of a process or method can occur through human interaction, pre-programmed computer control and response systems, or combinations thereof.

Method of Olefin Hydration

The method of olefin hydration for forming an associated alcohol product using a membrane-integrated hydration reactor includes the step of introducing an olefin feed composition into the production zone of a membrane-integrated hydration reactor. The olefin feed composition includes an olefin, the olefin comprising at least one isomer of butene. An embodiment of the method of olefin hydration includes introducing an olefin feed composition having only a single isomer of butene. An embodiment of the method includes introducing an olefin feed composition having mixed butenes. An embodiment of the method includes introducing an olefin feed composition having mixed olefins. An embodiment of the method includes introducing an olefin feed composition having at least 5% by weight iso-butene.

The method of olefin hydration for forming an associated alcohol product using a membrane-integrated hydration reactor includes the step of introducing water into the production zone of a membrane-integrated hydration reactor. The water and the olefin feed composition introduction into the membrane-integrated hydration reactor can occur separately or as a combined feed. An embodiment of the method of olefin hydration includes introducing the water and olefin feed composition separately into the production zone. An embodiment of the method includes pre-combining the water and the olefin feed composition before introducing the combination into the production zone of the membrane-integrated hydration reactor.

An embodiment of the method of olefin hydration includes introducing water and olefin feed composition to the membrane-integrated hydration reactor such that the stoichiometric feed ratio of water to olefins is in the range of from about 1:1 to about 10:1. For a membrane-integrated hydration reactor having more than one production zone, an embodiment of the method includes introducing the water and the olefin feed composition to the MIHR such that the stoichiometric feed ratio of water to olefins into a first production zone is different than the stoichiometric feed ratio of water to olefins into a second production zone. Reasons for using different stoichiometric feed ratios include varying catalytic activity between production zones, separations zone fluid level management, production zone pressure management and the amount of internal water conveyed between sets of production and separations zones in one-way fluid communication.

The method of olefin hydration for forming an associated alcohol product using a membrane-integrated hydration reactor includes the step of operating the membrane-integrated hydration reactor at olefin hydration process conditions such that an associated alcohol product forms from the olefin composition using water in the presence of the solid acid olefin hydration catalyst in the production zone. The associated alcohol includes at least one type of butanol. The one type of butanol includes TBA and SBA. An embodiment of the method includes operating the membrane-integrated hydration reactor such that the associated alcohol is mixed butanols. An embodiment of the method includes operating the membrane-integrated hydration reactor such that the associated alcohol also includes lower-carbon alcohols. Non-butanol alcohols include ethanol, propanols, pentanols and hexanols.

An embodiment of the method of olefin hydration includes operating the membrane-integrated hydration reactor at olefin hydration process conditions such that the stoichiometric ratio of water to olefins in the production zone is in a range of from about 1:1 to about 10:1.

An embodiment of the method of olefin hydration includes operating the membrane-integrated hydration reactor at olefin hydration process conditions such that the pressure in the production zone is in a range of from about 8 bars to about 70 bars. An embodiment of the method includes operating the membrane-integrated hydration reactor such that the pressure in the production zone is in a range of from about 10 bars to about 40 bars.

An embodiment of the method of olefin hydration includes operating the membrane-integrated hydration reactor at olefin hydration process conditions such that the temperature in the production zone is in a range of from about 50° C. to about 150° C. An embodiment of the method includes operating the membrane-integrated hydration reactor such that the temperature in the production zone is in a range of from about 90° C. to about 120° C.

The method of olefin hydration for forming an associated alcohol product using a membrane-integrated hydration reactor includes the step of operating the membrane-integrated hydration reactor such that the production zone product mixture comprising the associated alcohol and any unreacted water forms and that the production zone product mixture passes to the associated separations zone.

The method of olefin hydration includes the step of operating the membrane-integrated hydration reactor such that any unreacted water is selectively removed from the production zone product mixture, forming both the associated alcohol product and a pervaporated water product.

An embodiment of the method of olefin hydration includes operating the membrane-integrated hydration reactor at olefin hydration process conditions such that a pressure differential between the feed side and the permeate side of the hydrophilic membrane has a value in a range of from about 8 bars to about 70 bars differential. An embodiment of the method of olefin hydration includes operating the membrane-integrated hydration reactor such that the pressure on the permeate side of the hydrophilic membrane is less than atmospheric pressure.

The membrane-integrated hydration reactor produces the associated alcohol product. An embodiment of the method of olefin hydration includes producing an associated alcohol product that is substantially free of water by weight. An embodiment of the method includes producing an associated alcohol product that contains less than or equal to 0.5 weight percent water of the total associated alcohol product. An embodiment of the method includes producing an associated alcohol product that contains less than or equal to 100 parts-per-million by volume butenes in the total associated alcohol product.

An embodiment of the method of olefin hydration further includes the step of producing the pervaporated water product from the membrane-integrated hydration reactor. An embodiment of the method of olefin hydration further includes the step of producing the pervaporated water product such that it is introduced into a different production zone. An embodiment of the method of olefin hydration further includes the step of producing the pervaporated water product such that it is directly introduced into a production zone fluidly coupled to the permeate side of the hydrophilic membrane of the separation zone.

What is claimed is:

1. A membrane-integrated hydration reactor operable to produce an associated alcohol product from an olefin using water, the membrane-integrated hydration reactor comprising:
    a solid acid olefin hydration catalyst operable to convert the olefin into the associated alcohol product using water at olefin hydration process conditions;
    a hydrophilic membrane having a feed side and a permeate side, operable to selectively pervaporate water one-way from the feed side to the permeate side at olefin hydration process conditions, forming a pervaporated water product, and to prevent pervaporation of associated alcohol product and permeation of the olefin at olefin hydration conditions;
    a production zone containing the solid acid olefin hydration catalyst, operable to both receive an olefin feed containing the olefin and a water feed containing the water such that the olefin and the water intimately intermingle in the presence of the solid acid olefin hydration catalyst contained in the production zone and to form a production zone product mixture comprising the associated alcohol product and any unreacted water and pass the production zone product mixture to an associated separations zone;
    an olefin feed line in fluid communication with the production zone, such that the olefin feed line feeds the olefin feed to the production zone
    a water feed line in fluid communication with the production zone, such that the water feed line feeds water to the production zone; and
    the associated separations zone containing the hydrophilic membrane, fluidly coupling to the production zone such that the production zone directs the production zone product mixture to the feed side of the hydrophilic membrane, and is operable to form and produce both the associated alcohol product and the pervaporated water product from the production zone product mixture.

2. The membrane-integrated hydration reactor of claim 1 where the olefin feed line provides a single isomer of butene and the production zone forms the associated alcohol product as a single isomer of butanol.

3. The membrane-integrated hydration reactor of claim 1 where the olefin feed line provides a mixture of butene isomers and the production zone forms the associated alcohol product as a mixture of butanol isomers.

4. The membrane-integrated hydration reactor of claim 1 where the olefin feed line provides a mixture of lower-carbon olefins and the production zone forms the associated alcohol product as a mixture of lower-carbon alcohols.

5. The membrane-integrated hydration reactor of claim 1 where the production zone and the associated separations zone overlap within the reactor.

6. The membrane-integrated hydration reactor of claim 1 where the solid acid olefin hydration catalyst is a structured catalyst bed.

7. The membrane-integrated hydration reactor of claim 1 where the solid acid olefin hydration catalyst is integrated with the feed side surface of the hydrophilic membrane.

8. The membrane-integrated hydration reactor of claim 1 where the hydrophilic membrane comprises an inorganic material.

9. The membrane-integrated hydration reactor of claim 1 where the hydrophilic membrane comprises a polymeric material.

10. A membrane-integrated hydration reactor operable to produce an associated alcohol product from an olefin using water, the membrane-integrated hydration reactor comprising:
    a solid acid olefin hydration catalyst operable to convert the olefin into the associated alcohol product using water at olefin hydration process conditions;
    a hydrophilic membrane having a feed side and a permeate side, operable to selectively pervaporate water one-way from the feed side to the permeate side at olefin hydration process conditions, forming a pervaporated water product, and to prevent pervaporation of associated alcohol product and permeation of the olefin at olefin hydration conditions;

a production zone containing the solid acid olefin hydration catalyst, operable to both receive an olefin feed containing the olefin and a water feed containing the water such that the olefin and the water intimately intermingle in the presence of the solid acid olefin hydration catalyst contained in the production zone and to form a production zone product mixture comprising the associated alcohol product and any unreacted water and pass the production zone product mixture to an associated separations zone;

the associated separations zone containing the hydrophilic membrane, fluidly coupling to the production zone such that the production zone directs the production zone product mixture to the feed side of the hydrophilic membrane, and is operable to form and produce both the associated alcohol product and the pervaporated water product from the production zone product mixture; and an internal condenser operable to condense into a liquid the pervaporated water product on the permeate side of the hydrophilic membrane.

11. The membrane-integrated hydration reactor of claim 1 where the membrane-integrated hydration reactor is operable to maintain separate operating conditions between the production zone and the associated separations zone.

12. The membrane-integrated hydration reactor of claim 1 where the membrane-integrated hydration reactor comprises more than one production zone and more than one associated separations zones.

13. The membrane-integrated hydration reactor of claim 12 where the membrane-integrated hydration reactor is operable to maintain separate operating conditions between a first set of production and associated separations zones and a second set of production and associated separations zones, where the first associated separations zone is fluidly coupled to and in one-way fluid communications with the second production zone.

14. The membrane-integrated hydration reactor of claim 1 where the olefin feed line comprises fresh olefins and recovered olefins, wherein the recovered olefins are recovered from a recycle olefin feed line.

15. The membrane-integrated hydration reactor of claim 1 where the water feed line comprises make-up water from a water make-up feed line and recycled water from a water recycle line.

16. The membrane-integrated hydration reactor of claim 1 further comprising an internal condenser operable to condense into a liquid the pervaporated water product on the permeate side of the hydrophilic membrane.

17. A membrane-integrated hydration reactor operable to produce an associated alcohol product from an olefin using water, the membrane-integrated hydration reactor comprising:

a solid acid olefin hydration catalyst operable to convert the olefin into the associated alcohol product using water at olefin hydration process conditions;

a hydrophilic membrane having a feed side and a permeate side, operable to selectively pervaporate water one-way from the feed side to the permeate side at olefin hydration process conditions, forming a pervaporated water product, and to prevent pervaporation of the associated alcohol product and permeation of the olefin at olefin hydration conditions;

a production zone containing the solid acid olefin hydration catalyst, operable to both receive an olefin feed containing the olefin and a water feed containing the water such that the olefin and the water intimately intermingle in the presence of the solid acid olefin hydration catalyst contained in the production zone and to form a production zone product mixture comprising the associated alcohol product and any unreacted water and pass the production zone product mixture to an associated separations zone; and the associated separations zone containing the hydrophilic membrane, fluidly coupling to the production zone such that the production zone directs the production zone product mixture to the feed side of the hydrophilic membrane, and is operable to form and produce both the associated alcohol product and the pervaporated water product from the production zone product mixture, where the membrane-integrated hydration reactor comprises more than one production zone and more than one associated separations zones and where the more than one production zones and the more than one associated separations zones are alternating in series and fluidly couple to permit one-way fluid communications through the alternating series of production zones and associated separations zones, where the fluid of communication is water.

18. The membrane-integrated hydration reactor of claim 13 such that in the alternating series of fluidly coupled more than one production zones and more than one associated separations zones a first production zone is operable to communicate fluid one-way to all of the remaining production zones and all of the separations zones and such that a last separations zone in the alternating series is operable to receive fluid communicated one-way from all of the production zones and all of the remaining separations zones.

19. The membrane-integration hydration reactor of claim 13 such that in the alternating series of fluidly coupled more than one production zones and more than one associated separations zones a first production zone is in direct fluid contact only with one associated separations zone and a last separations zone in the alternating series is in direct fluid contact only with one production zone, the other production zones being in direct fluid contact with more than one separations zones and the other separations zones being in direct fluid contact with more than one production zones.

* * * * *